(12) United States Patent
Boiocchi

(10) Patent No.: US 12,102,701 B2
(45) Date of Patent: Oct. 1, 2024

(54) ORAL CARE PRODUCT

(71) Applicant: CURASEPT A.D.S. S.R.L., Saronno (IT)

(72) Inventor: Lorenzo Emiliano Boiocchi, Milan (IT)

(73) Assignee: CURASEPT A.D.S. S.R.L., Saronno (IT)

( * ) Notice: Subject to any disclaimer, the term of this patent is extended or adjusted under 35 U.S.C. 154(b) by 0 days.

(21) Appl. No.: 17/435,314

(22) PCT Filed: Feb. 27, 2020

(86) PCT No.: PCT/EP2020/055199
§ 371 (c)(1),
(2) Date: Aug. 31, 2021

(87) PCT Pub. No.: WO2020/178148
PCT Pub. Date: Sep. 10, 2020

(65) Prior Publication Data
US 2022/0117868 A1    Apr. 21, 2022

(30) Foreign Application Priority Data

Mar. 1, 2019   (IT) .................. 102019000003009

(51) Int. Cl.
*A61K 8/43* (2006.01)
*A61K 8/23* (2006.01)
*A61K 8/60* (2006.01)
*A61K 8/67* (2006.01)
*A61K 8/81* (2006.01)
*A61Q 11/00* (2006.01)

(52) U.S. Cl.
CPC .................. *A61K 8/43* (2013.01); *A61K 8/23* (2013.01); *A61K 8/606* (2013.01); *A61K 8/676* (2013.01); *A61K 8/8182* (2013.01); *A61Q 11/00* (2013.01)

(58) Field of Classification Search
CPC .......... A61Q 11/00; A61K 8/676; A61K 8/43; A61K 8/23; A61K 8/042; A61K 8/8182; A61K 8/606
See application file for complete search history.

(56) References Cited

U.S. PATENT DOCUMENTS 5,662,889 A    9/1997   Vainberg et al.

FOREIGN PATENT DOCUMENTS

| EP | 0712936 A1 | 5/1996 |
| EP | 1340490 A1 | 9/2003 |
| EP | 2614812 A1 | 7/2013 |
| JP | H0558866 A | 3/1993 |
| JP | 2006219431 | * 8/2006 |
| JP | 2017178906 | * 10/2017 |
| JP | 2018203628 A | 12/2018 |
| WO | WO 2016112998 | * 7/2016 |

OTHER PUBLICATIONS

PCT International Search Report and Written Opinion from corresponding Application No. PCT/EP2020/055199 mailed Jun. 5, 2020.
PCT Written Opinion from corresponding Application No. PCT/EP2020/055199 mailed Feb. 21, 2021.
PCT International Preliminary Report on Patentability from corresponding Application No. PCT/EP2020/055199 mailed Jun. 16, 2021.

* cited by examiner

*Primary Examiner* — Lezah Roberts
(74) *Attorney, Agent, or Firm* — SILVIA SALVADORI, P.C.; Silvia Salvadori

(57) ABSTRACT

The present invention relates to an oral care product, such as a mouthwash, periodontal gel or a toothpaste comprising chlorhexidine and sodium DNA. Said oral care product presents an antibacterial effect effective against gingivitis, bacterial plaque and periodontitis combined with a healing and anti-inflammatory activity and which, moreover, counteracts the oxidative stress so as to limit the onset and the progression of irritations of the oral mucosae and promote their trophism.

17 Claims, 4 Drawing Sheets

ORAL CARE PRODUCT

CROSS REFERENCE TO RELATED APPLICATION

This application claims benefit under 35 U.S.C. § 371 to international application No. PCT/EP2020/055199 filed on Feb. 27, 2020, which claims priority to Italian application No. 102019000003009 filed Mar. 1, 2019, the contents of which are incorporated by reference in their entireties.

FIELD OF THE INVENTION

The present invention relates to an oral care product based on chlorhexidine and sodium DNA, such as for example a mouthwash, a periodontal gel or a toothpaste, which prevents the formation of plaque on the teeth and, at the same time, limits the onset and the progression of irritations of the oral mucosa, thus promoting their trophism.

STATE OF THE ART

Chlorhexidine-based oral care products, such as mouthwashes, have been known for some time, since this active component is a powerful antibacterial thanks to its ability to penetrate the external membrane of bacteria and coagulate the internal proteins thereof. Chlorhexidine also carries out an intense anti-plaque activity. The solutions containing chlorhexidine in various concentrations are also used to prevent postoperative complications.

However, it is known that the prolonged use of chlorhexidine-based oral care products can for example cause irritation of the oral mucosae which, in the long run, can deteriorate their correct trophism.

The Applicant has in fact found that although the beneficial effects of chlorhexidine in the treatment of gingivitis, bacterial plaque and periodontitis are known, reservations remain with regard to its use for these treatments, especially for long-term treatments, deriving from the awareness of the side effects caused by said active component on the oral mucosae.

SUMMARY OF THE INVENTION

The aim of the present invention is therefore to provide a new oral care product comprising chlorhexidine, effective against gingivitis, bacterial plaque and periodontitis and having a healing and anti-inflammatory activity and which also counteracts oxidative stress, so as to limit the onset and the progression of irritations and alterations of the cellular structure of the oral mucosae resulting from the use of chlorhexidine, and thus promote the trophism of the oral mucosae themselves.

In accordance with the present invention, the Applicant has surprisingly found that these desired characteristics can be achieved by using, in combination with chlorhexidine, sodium DNA.

Therefore, the present invention relates to an oral care product comprising chlorhexidine and sodium DNA.

It has indeed been surprisingly discovered that the association of sodium DNA with chlorhexidine not only counteracts the irritating effect of the latter on the oral mucosae, exerting a protective effect on the latter and a healing effect on possible wounds in the oral cavity, but also allows limiting the side effects of prolonged use of chlorhexidine-based oral care products, which include alterations of the cellular structure, including vacuolisation, degeneration of the cell nucleus, and expansion of intercellular spaces.

Thanks to the specific combination of sodium DNA and chlorhexidine, the oral care product according to the present invention therefore has a range of properties capable of overcoming the application and functional limits of oral care products based on chlorhexidine only, expanding the application possibilities and remedying some side effects of their prolonged use.

The oral care product according to the present invention is in fact able to associate an effective protective action at the cellular level towards the side effects of chlorhexidine, thus limiting the onset and the progression of alterations of the cellular structure of the oral mucosae, with an antibacterial effect effective against gingivitis, bacterial plaque and periodontitis combined with a healing and anti-inflammatory activity able to counteract oxidative stress, and to limit the onset and the progression of irritations of the oral mucosae, thus promoting their trophism. These characteristics make its use particularly advantageous, even in the long term, without encountering the onset of the irritating effect and side effects at the cellular level of chlorhexidine on the oral mucosae.

The Applicant has in particular noticed that one of the application and functional limits to the use of chlorhexidine-based oral care products resides in the onset—especially in the case of prolonged use—of side effects that entail, in addition to irritation of the oral mucosae, also alterations at the level of the cellular structure of said mucosae, including vacuolisation, degeneration of the cell nucleus, and expansion of the intercellular spaces.

The Applicant has therefore surprisingly discovered that the association of sodium DNA with chlorhexidine not only counteracts its irritating effect on the oral mucosae, exerting a protective effect on them and a healing effect on possible wounds of the oral cavity, but also allows limiting the side effects of the prolonged use of said active component, which include alterations of the cellular structure, including vacuolisation, degeneration of the cell nucleus, and expansion of the intercellular spaces.

This allowed the Applicant to define and develop a new oral care product comprising chlorhexidine, therefore effective against gingivitis, bacterial plaque and periodontitis, which was at the same time unable to give rise to, or severely limit, the side effects of prolonged use of said active component, which include irritations and even alterations of the cellular structure of the oral mucosae, including vacuolisation, degeneration of the cell nucleus, and expansion of the intercellular spaces.

In a preferred embodiment thereof, said oral care product is selected from the group consisting of: mouthwash, periodontal gel, and toothpaste.

In a preferred embodiment thereof, the oral care product according to the present invention is a mouthwash comprising from 0.01% to 0.30% by weight of chlorhexidine, from 0.01% to 0.2% by weight of sodium DNA, from 0.1% to 0.5% by weight of at least one metabisulfite salt of an alkaline or alkaline earth metal, from 0.1% to 1.0% by weight ascorbic acid, from 0.05% to 1% by weight of at least one polyvinylpyrrolidone-vinylacetate copolymer, with respect to the total volume of the mouthwash.

In a further aspect, the present invention relates to sodium DNA for use in a method for the treatment of a pathology of the oral mucosa, wherein said pathology entails an alteration of the cellular structure of said oral mucosa, said alteration of the cellular structure being selected in the group consisting of: vacuolisation, degeneration of the cell nucleus, expansion of the intercellular spaces.

In fact, it has surprisingly been discovered that sodium DNA exerts a protective action on the cellular structure of the oral mucosa, able to counteract the onset and the progression of its alterations, including vacuolisation, degeneration of the cell nucleus, and expansion of intercellular spaces.

This allows to therapeutically intervene on cellular alterations of the oral mucosa of any etiology, for example by limiting the side effects of treatments with active components that are particularly aggressive towards the cellular structure of the oral mucosae, such as chlorhexidine.

The Applicant has found that the treatment of the side effects of chlorhexidine constitutes an innovative aspect of particular value in light of the aforementioned application and functional limits for the use of chlorhexidine-based oral care products.

In a further aspect thereof, the present invention therefore also relates sodium DNA for use in a method for the treatment of the side effects of chlorhexidine in a patient undergoing treatment with chlorhexidine, wherein said side effects entail an alteration of the cellular structure of the oral mucosa of said patient, said alteration of the cellular structure being selected in the group consisting of:

vacuolisation, degeneration of the cell nucleus, expansion of the intercellular spaces.

DETAILED DESCRIPTION OF THE INVENTION

Figure 1:
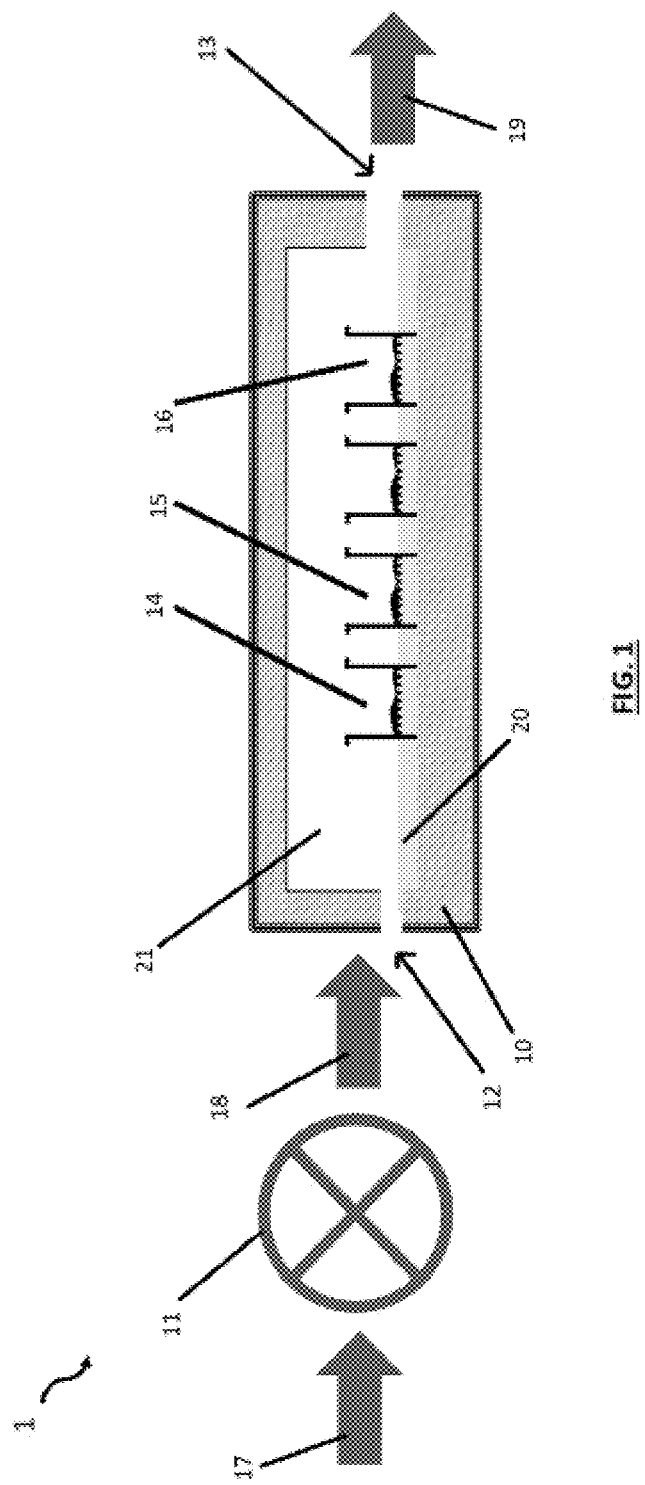
FIG. 1 shows a not to scale cross-sectional schematic view of the system used for experimentation according to Example 1.

The present invention can be presented in one or more of its aspects or one or more of the preferred characteristics reported below, which can be combined with one another as preferred according to the application requirements.

Within the context of the present description and following claims, all the numerical magnitudes indicating amounts, parameters, percentages, and so on are to be considered preceded in every circumstance by the term "about" unless indicated otherwise. Further, all the ranges of numerical magnitudes include all the possible combinations of maximum and minimum numerical values and all the possible intermediate ranges, as well as those indicated below.

Within the scope of the present invention, a combination of two substances has been identified, chlorhexidine and sodium DNA, whose combined antibacterial, healing and anti-inflammatory and oxidative stress contrasting characteristics make their use as active components of an oral care product particularly effective against gingivitis, bacterial plaque and periodontitis which, at the same time, limits the onset and the progression of irritations and alterations of the cellular structure of the oral mucosae resulting from the use of chlorhexidine, and thus promote the trophism of the oral mucosae themselves.

More particularly, the present invention relates to an oral care product comprising chlorhexidine and sodium DNA.

In the present invention when the expression is used:

"% by weight with respect to the total volume of the mouthwash" means the amount in grams of a given component present in 100 milliliters (mL) of mouthwash;

"chlorhexidine" means, unless otherwise specified, the compound 1,1'-hexamethylenebis[5-(p-chlorphenyl)biguanide], a salt or complex thereof;

"sodium DNA" means the sodium salt of deoxyribonucleic acid, for example obtainable by extraction of native deoxyribonucleic acid from the tissue of the male sturgeon gonads and subsequently purified, depolymerized and neutralized with sodium ions.

Without wanting to be bound to a specific theory, it is believed that the association of sodium DNA with chlorhexidine not only counteracts the irritating effect of the latter on the oral mucosae, exerting a protective effect on them and a healing effect of possible wounds of the oral cavity, but also allows limiting the side effects of prolonged use of chlorhexidine-based oral care products, which include alterations of the cell structure, including vacuolisation, degeneration of the cell nucleus, and expansion of the intercellular spaces.

The Applicant has in particular noticed that one of the application and functional limits to the use of chlorhexidine-based oral care products resides in the onset—especially in the case of prolonged use—of side effects that entail, in addition to irritation of the oral mucosa, also alterations at the level of the cellular structure of said mucosae, including vacuolisation, degeneration of the cell nucleus, and expansion of the intercellular spaces.

The Applicant has therefore surprisingly discovered that the association of sodium DNA with chlorhexidine not only counteracts its irritating effect on the oral mucosae, exerting a protective effect on them and a healing effect on possible wounds of the oral cavity, but also allows limiting the side effects of the prolonged use of said active component, which include alterations of the cellular structure, including vacuolisation, degeneration of the cell nucleus, and expansion of the intercellular spaces.

This allowed the Applicant to define and develop a new oral care product comprising chlorhexidine, therefore effective against gingivitis, bacterial plaque and periodontitis, which was at the same time unable to give rise to, or severely limit, the side effects of prolonged use of said active component, which include irritations and even alterations of the cellular structure of the oral mucosae, including vacuolisation, degeneration of the cell nucleus, and expansion of the intercellular spaces.

Thanks to the specific combination of sodium DNA and chlorhexidine, the oral care product according to the present invention therefore has a range of properties capable of overcoming the application and functional limits of oral care products based on chlorhexidine only, expanding the application possibilities and remedying some side effects of their prolonged use.

The oral care product according to the present invention is in fact able to associate an effective protective action at the cellular level towards the side effects of chlorhexidine, thus limiting the onset and the progression of alterations of the cellular structure of the oral mucosae, with an antibacterial effect effective against gingivitis, bacterial plaque and periodontitis combined with a healing and anti-inflammatory activity able to counteract oxidative stress, and limit the onset and the progression of irritations of the oral mucosae, thus promoting their trophism. These characteristics make its use particularly advantageous, even in the long term, without encountering the onset of the irritating effect and side effects at the cellular level of chlorhexidine on the oral mucosae.

In a preferred embodiment thereof, said oral care product is selected from the group consisting of: mouthwash, periodontal gel, and toothpaste.

In a first preferred embodiment thereof, the oral care product according to the present invention is a mouthwash comprising chlorhexidine and sodium DNA.

The mouthwash according to the present invention comprises chlorhexidine. Preferably, the amount of chlorhexidine in the mouthwash is in the range from 0.01% to 0.30% by weight, more preferably from 0.05% to 0.30% by weight, even more preferably from 0.09% to 0.20% by weight, with respect to the total volume of the mouthwash.

In the mouthwash according to the present invention, chlorhexidine can advantageously also be present in the form of salt and complex. Preferably, the mouthwash according to the present invention comprises chlorhexidine in the form of salt or complex. As chlorhexidine salt, for example, chlorhexidine digluconate or chlorhexidine diacetate can be used in the mouthwash according to the present invention. Preferably, the mouthwash according to the present invention comprises chlorhexidine in the form of chlorhexidine gluconate.

The mouthwash according to the present invention comprises sodium DNA.

Preferably, in the mouthwash the amount of sodium DNA is in the range from 0.01% to 0.2%, more preferably from 0.05% to 0.1%, by weight with respect to the total volume of the mouthwash.

Sodium DNA suitable for the purposes of the present invention is commercially available, for example the one marketed under the name Kalinat aw powder (Kalichem). Said amount of sodium DNA has in fact proved to be optimal for counteracting the irritating effect of chlorhexidine on the oral mucosae, exerting a protective effect on them and a healing effect on possible wounds of the oral cavity, thus also promoting a correct trophism of the oral mucosae themselves.

Preferably, the mouthwash according to the present invention comprises at least one metabisulfite salt of an alkaline or alkaline earth metal.

The presence of at least one metabisulfite salt of an alkaline or alkaline earth metal counteract the drawback of dark pigmentation on teeth, a side effect of chlorhexidine.

Preferably, the at least one metabisulfite salt of an alkaline or alkaline earth metal is selected from the group which consists of: sodium metabisulfite, potassium metabisulfite, calcium metabisulfite. More preferably, the mouthwash according to the present invention comprises sodium metabisulphite.

Preferably, in the mouthwash according to the present invention the amount of the at least one metabisulfite salt of an alkaline or alkaline earth metal is in the range from 0.1% to 0.5%, more preferably from 0.15% to 0.3% by weight with respect to the total volume of the mouthwash.

Preferably, the mouthwash according to the present invention comprises ascorbic acid.

Preferably, in the mouthwash according to the present invention the amount of ascorbic acid is in the range from 0.1% to 1.0% by weight, with respect to the total volume of the mouthwash.

The presence of ascorbic acid counteracts the drawback of dark pigmentation on teeth, a side effect of chlorhexidine.

Preferably, the mouthwash according to the present invention comprises ascorbic acid and at least one metabisulfite salt of an alkaline or alkaline earth metal, even more preferably from 0.1% to 0.5% by weight of at least one metabisulfite salt of an alkaline or alkaline earth metal and from 0.1% to 1.0% by weight of ascorbic acid, with respect to the total volume of the mouthwash.

Said combination of components in said amounts proved to be optimal for counteracting the side effect of chlorhexidine of the dark pigmentation on teeth.

Preferably, the mouthwash according to the present invention comprises tribasic sodium citrate.

Preferably, in the mouthwash according to the present invention the amount of sodium tribasic citrate is in the range from 0.8% to 2.0%, more preferably from 0.8% to 1.2%, by weight with respect to the total volume of the mouthwash.

The presence of tribasic sodium citrate in said amounts advantageously allows regulating the pH of the mouthwash to optimal values for its use.

In a preferred embodiment, the mouthwash according to the present invention comprises ascorbic acid and tribasic sodium citrate. More preferably, the mouthwash according to the present invention comprises from 0.1% to 1% by weight with respect to the total volume of the ascorbic acid in the mouthwash and from 0.8% to 2.0% by weight with respect to the total volume of the tribasic sodium citrate mouthwash.

It has in fact surprisingly been discovered that said combination of ascorbic acid and tribasic sodium citrate allows stabilizing the formulation of the mouthwash according to the present invention.

Preferably, the mouthwash according to the present invention comprises at least one polyvinylpyrrolidone-vinylacetate copolymer. Polyvinylpyrrolidone-vinylacetate copolymers suitable for the purposes of the present invention are commercially available, for example those marketed under the name Luviskol® (BASF SE).

The at least one polyvinylpyrrolidone-vinylacetate copolymer advantageously exerts a film-forming and anti-plaque action in the mouthwash according to the present invention.

Preferably, in the mouthwash according to the present invention the amount of the at least one polyvinylpyrrolidone-vinylacetate copolymer is in the range from 0.05% to 1%, more preferably from 0.3% to 1%, by weight with respect to the total volume of the mouthwash.

In a preferred embodiment thereof, the oral care product according to the present invention is a mouthwash comprising from 0.01% to 0.30% by weight of chlorhexidine, from 0.01% to 0.2%, more preferably from 0.01% to 0.1%, by weight of sodium DNA, from 0.1% to 0.5% by weight of at least one metabisulfite salt of an alkaline or alkaline earth metal, from 0.1% to 1.0% by weight ascorbic acid, from 0.05% to 1%, more preferably from 0.3% to 1%, by weight of at least one polyvinylpyrrolidone-vinylacetate copolymer, with respect to the total volume of the mouthwash.

The mouthwash according to the invention can contain one or more of the other possible ingredients known in the art for solutions for oral care.

In particular, the mouthwash according to the present invention can further comprise one or more additives selected from the group which consists of: sweeteners, flavourings, wetting agents, preservatives, emulsifiers, pH regulators, food colouring.

As sweeteners, the mouthwash according to the present invention can for example comprise xylitol, sodium saccharinate, potassium acesulfame, sucralose, *stevia* extract.

As flavourings, the mouthwash according to the present invention can for example comprise peppermint, menthol, anethole, *Mentha viridis*, cinnamon, cloves, eucalyptol.

As wetting agents, the mouthwash according to the present invention can for example comprise propylene glycol, sorbitol, glycerin As preservatives, the mouthwash according to the present invention can for example comprise sodium benzoate, methylisothiazolinone.

As solubilizing surfactants, the mouthwash according to the present invention can for example comprise: hydrogenated castor oil Peg 40, Poloxamer 407.

As pH regulators, the mouthwash according to the present invention can for example comprise sodium citrate, citric acid.

As colourings, the mouthwash according to the present invention can for example comprise CI 19140, CIU 42090, CI 17200.

The mouthwash according to the invention is conveniently prepared in a known way in the form of solution or suspension in a suitable solvent medium, preferably water.

According to a preferred embodiment, the mouthwash according to the invention comprises the following components:
1. Water
2. Xylitol
3. Propylene glycol
4. Hydrogenated castor oil PEG 40
5. Ascorbic acid
6. Chlorhexidine digluconate
7. Polyvinylpyrrolidone-vinylacetate copolymer
8. Sodium DNA
9. Flavouring
10. Poloxamer 407
11. Sodium metabisulfite
12. Sodium citrate
13. Citric acid
14. C.I. 42090
15. C.I. 17200

In a further preferred embodiment, the oral care product according to the present invention is a periodontal gel comprising chlorhexidine and sodium DNA.

According to a preferred embodiment, the periodontal gel according to the invention comprises the following components:
1. Water
2. Propylene glycol
3. Hydroxyethyl cellulose
4. Polyvinylpyrrolidone-vinylacetate copolymer
5. Hydrogenated castor oil PEG 40
6. Chlorhexidine digluconate
7. Sodium acetate
8. Sodium DNA
9. Menthol
10. Peppermint oil
11. Acetic acid
12. Sodium metabisulfite
13. Ascorbic acid Preferably, the periodontal gel according to the present invention comprises from 0.5% by weight to 1.0% by weight of chlorhexidine, with respect to the total volume of the periodontal gel.

Preferably, the periodontal gel according to the present invention comprises sodium DNA in a maximum amount of 0.3%, more preferably from 0.01% to 0.3%, by weight with respect to the total weight of the periodontal gel.

In a still further preferred embodiment, the oral care product according to the present invention is a toothpaste comprising chlorhexidine and sodium DNA.

According to a preferred embodiment, the toothpaste according to the invention comprises the following components:
1. Sorbitol
2. Water
3. Silica (Hydrated silica)
4. Glycerol
5. Xylitol
6. Cocamidopropyl betaine
7. Polyvinylpyrrolidone-vinylacetate copolymer
8. Hydrogenated castor oil PEG 40
9. Flavouring
10. Chlorhexidine digluconate
11. Carboxymethyl cellulose
12. Ascorbic acid
13. Sodium metabisulfite
14. Sodium DNA
15. Sodium saccharin
16. Sodium benzoate
17. Sodium citrate Preferably, the toothpaste according to the present invention comprises from 0.05% by weight to 0.2% by weight of chlorhexidine, with respect to the total volume of the toothpaste.

Preferably, at least one inorganic fluoride can optionally be present in the toothpaste according to the invention.

Preferably, in the toothpaste according to the present invention the amount of sodium DNA is in the range from 0.01% to 0.05% by weight with respect to the total volume of the toothpaste.

In a further aspect, the present invention also refers to the use of the oral care product according to the present invention as an anti-irritation agent of the oral mucosa.

In a further aspect, the present invention also refers to the use of the oral care product according to the present invention as a healing agent of the oral mucosa.

Preferably, said oral mucosa comprises the periodontal tissue.

In fact, it has been discovered that, thanks to the association of sodium DNA with chlorhexidine, the oral care product according to the present invention counteracts the irritating effect of the latter on the oral mucosae, exerting a protective effect on them and a healing effect on possible wounds of the oral cavity.

It has also been found that the association of sodium DNA with chlorhexidine also allows limiting the side effects of prolonged use of chlorhexidine-based oral care products, which include alterations of the cellular structure, including vacuolisation, degeneration of the cell nucleus, and expansion of the intercellular spaces, thereby obviating one of the application and functional limits of said products.

Preferably, the present invention therefore also refers to the use of the oral care product according to the present invention in a method for the treatment of at least one pathology selected in the group which consists of: gingivitis, bacterial plaque, and periodontitis.

In addition, it has surprisingly been discovered that the oral care product according to the present invention is also effective in the treatment of peri-implant mucositis. Therefore in a further aspect thereof, the present invention also relates to the use of the oral care product according to the present invention in a method for the treatment of peri-implant mucositis.

In a further aspect thereof, the present invention relates to the use of sodium DNA for use in a method for the treatment of a pathology of the oral mucosa, wherein said pathology entails an alteration in the cellular structure of said oral mucosa, said alteration of the cellular structure being selected in the group consisting of: vacuolisation, degeneration of the cell nucleus, expansion of the intercellular spaces.

In fact, it has surprisingly been discovered that sodium DNA exerts a protective action on the cellular structure of the oral mucosa, able to counteract the onset and the progression of its alterations, including vacuolisation, degeneration of the cell nucleus, and expansion of intercellular spaces.

Preferably, said oral mucosa comprises the periodontal tissue.

The Applicant has also discovered that said protective action of the sodium DNA allows to therapeutically intervene on cellular alterations of the oral mucosa of any etiology, for example by limiting the side effects of treatments with active components that are particularly aggressive towards the cellular structure of the oral mucosae, such as example chlorhexidine.

The Applicant has found that the treatment of the side effects of chlorhexidine constitutes an innovative aspect of particular value in light of the aforementioned application and functional limits for the use of chlorhexidine-based oral care products.

In a further aspect thereof, the present invention therefore also relates sodium DNA for use in a method for the treatment of the side effects of chlorhexidine in a patient undergoing treatment with chlorhexidine, wherein said side effects entail an alteration of the cellular structure of the oral mucosa of said patient, said alteration of the cellular structure being selected in the group consisting of: vacuolisation, degeneration of the cell nucleus, expansion of the intercellular spaces.

Preferably, said oral mucosa comprises the periodontal tissue.

EXPERIMENTAL PART

The invention is now described by means of some examples to be considered for non-limiting illustrating purposes thereof.

Example 1

Materials and Methods

All the reagents, culture media and disposable materials used were obtained from Merck (E.Merck AG, Darmstadt, Germany). Samples of reconstituted human oral epithelium (henceforth "ROE") of 0.5 cm$^2$ (SkinEthic HOE™/Human oral epithelium) were obtained from EPISKIN (EPISKIN, Lyon Cedex 7, France). The sodium DNA (henceforth "NaDNA", Kalinat® AW) was obtained from KALICHEM (Kalichem, Brescia, Italy).

The following mouthwash solutions, containing no preservatives, were tested:
A. mouthwash containing 0.2% by weight of chlorhexidine, with respect to the total volume of the mouthwash (positive control);
B. mouthwash containing 0.2% by weight of chlorhexidine and 0.01% by weight of NaDNA, with respect to the total volume of the mouthwash (test);
C. mouthwash containing 0.01% by weight of NaDNA, with respect to the total volume of the mouthwash);
D. phosphate buffered saline solution (PBS, negative control).

Reconstituted Human Oral Epithelium (ROE)

32 ROE samples were used. The ROE samples were opened under the hood in the presence of a sterile air flow. The samples were arranged in 24-well transport plates containing medium with agarose nutrient. The samples were extracted from the transport plates and the agarose was removed. Then the samples were placed in 6-well plates with nutrient medium (RPMI 1640 medium, supplemented with 20% fetal bovine serum, 1% L-glutamine and 1% penicillin/streptomycin). Before the test, the culture plates were incubated overnight at 37° C. in a $CO_2$ atmosphere at 5% and 100% relative humidity.

Bioreactor

The tests were carried out in two commercially available Drip Flow bioreactors (DFR 110; BioSurface Technologies, Bozeman, MT, USA) adapted to be able to position the trays containing the samples on the bottom of the flow cells and to be able to immerse the ROE samples in the surrounding circulating medium. This allowed the use of nutrient medium at a continuous flow rate.

All trays of bioreactors containing test tubes and samples were sterilized before the start of the experiment using a chemiclave with hydrogen peroxide gas plasma technology (Sterrad, ASP, Irvine, CA, USA). By limiting the maximum temperature to 45° C., damages caused by the heat of the entire system were avoided. After sterilization, the bioreactors were then assembled inside a sterile hood.

Test Procedures

FIG. 1 shows a not to scale cross-sectional schematic view of the system used for the experimentation, showing by way of example one of the two bioreactors. The system 1 comprises a peristaltic pump 11, a reactor 10 of the Drip Flow type and flow cells 14, 15 and 16 containing the samples. The reactor 10 of the Drip Flow type is equipped with a flow chamber 21, an inlet 12 and a drain 13. The flow chamber 21 is configured to contain a flow medium 20.

The ROE samples were cut out from their support using sterile scalpels and tweezers and placed inside the bioreactors in eight flow cells 14, 15 and 16 of polytetrafluoroethylene (PTFE) containing four holes each, which fixed them and exposed their surfaces to the flow medium 20 comprising a nutrient medium (medium RPMI 1640, supplemented with 20% fetal bovine serum, 1% L-glutamine and 1% penicillin/streptomycin). All trays were fixed to the bottom of each flow chamber 21 of the two bioreactors 10 operating in parallel and immediately inoculated with new nutrient medium. The bioreactors were then transferred to an incubator operating at 37° C., at 5% $CO_2$ and at 100% of relative humidity. Then a computer-controlled multi-channel peristaltic pump 11 (RP-1, Rainin, Emeryville, CA, USA) was turned on, set at a flow rate of 9.6 ml/h and used to provide a constant flow of flow medium 20 comprising nutrient medium through the flow cells. In FIG. 1, arrows 17, 18 and 19 schematically indicate the flow direction of the flow medium 20. The peristaltic pump 11 feeds through the inlet 12 of the reactor 10 the flow medium 20 into the flow chamber 21 of the two bioreactors 10, which is then drained through the drain 13.

After 24 hours, the pump 11 was stopped and four flow cells 14, 15 and 16 were respectively treated with the mouthwash solutions A, B, C and D, one for each flow cell (10 ml). In each flow cell, two samples were treated for 5 minutes and the other two for 30 minutes by tilting the bioreactor 10 for 25 minutes, so that the solution completely covered the two lower samples, then bringing it back to the horizontal position for the remaining 5 minutes so as to cover all four samples. The remaining four flow cells 14, 15 and 16 were first treated with a 3% solution of $H_2O_2$ for 1 minute to induce a high oxidative stress and cell damage, then the samples were thoroughly rinsed with sterile PBS for 1 minute and the flow cells 14, 15 and 16 were treated with the mouthwash solutions tested as previously specified. Again, in each flow cell, two samples were treated with the mouthwash solutions for 5 minutes and the other two for 30 minutes.

After that, the pump 11 was reactivated for washing the mouthwash solutions for 60 minutes, then all the ROE samples were extracted from the flow cells 14, 15 and 16, immediately cut into 4 equal parts using sterile scalpels and tweezers and worked as follows.

Evaluation of the Samples

The ROE samples of each treatment were subjected to MTT viability tests (n=4), confocal laser scanning microscopy imaging (CLSM) (n=2) and histological evaluation (n=2) using optical microscopy and electron microscopy in imaging transmission (TEM).

MTT Viability Test

Cell survival was evaluated by MTT viability test. The dosage was carried out as follows: two starting stock solutions were prepared by dissolving 5 mg/ml of 3-(4,5-dimethylthiazol-2-yl)-2,5-diphenyltetrazolium bromide (MTT) in sterile PBS and 0.3 mg/ml of N-methylphenazinium methyl sulfate (PMS) in sterile PBS. The solutions were stored at 2° C. in light-resistant vials until the day of the experiment, when a new measurement solution (FMS) was made by mixing in a 1:1:8 ratio, respectively, MTT stock solution, sterile PMS and PBS stock solution. A lysis solution (LS) was prepared by dissolving 10% v/v of sodium dodecyl sulfate and 50% v/v of dimethylformamide in distilled water. The ROE samples subjected to MTT test were placed within the wells of a 24-well sterile flat-bottom plate. After that, 1 ml of FMS was pipetted into each well and the plates were incubated at 37° C. under light conditions for 1 hour. During incubation, the transport of electrons through the cell membrane and, to a lesser extent, the cellular oxide-reduction systems converted the MTT yellow salt into insoluble purple formazan. The conversion was facilitated by the intermediate electron acceptor (PMS). The unreacted FMS was then gently removed from the wells by aspiration and the formazan crystals were dissolved by adding 1 ml of LS into each well, followed by further incubation under ambient light conditions for 1 hour. A total of 100 microliters of the suspension was then removed from each well and the optical density (at 550 nm) was measured with a spectrophotometer (Genesys 10-S, Thermo Spectronic, Rochester, NY, USA).

CLSM Observations

CLSM imaging was performed using Live/Dead staining as described in Brambilla E, Ionescu A, Mazzoni A, Cadenaro M, Gagliani M, Ferraroni M, Tay F, Pashley D, Breschi L. (2014) Hydrophilicity of dentin bonding systems influences in vitro Streptococcus mutans biofilm formation. Dent Mater. 30(8): 926-35. In short, the ROE samples subjected to CLSM observations were stained using the LIVE/DEAD® Viability Kit for microscopy (Invitrogen Ltd., Paisley, UK). Cell fluorescence stained live was observed using a CLSM (Eclipse Ti2 inverted CLSM, Nikon, Tokyo, Japan). Four randomly selected image stack sections were recorded for each ROE sample. The confocal images were obtained using a dry Plan Apochromat 20× (NA 0.75) lens and digitized using Nikon's proprietary software, with a resolution of 1024×1024 pixels, with a 1.0 zoom factor. For each section of image stacks, 3D rendering reconstructions were obtained using the Drishti 3D software, as described in Lindhe J, Heyden G, Svanberg G, Löe H, Rindom Schott C. (1970). Effect of local applications of chlorhexidine on the oral mucosa of the hamster. J. Periodont. Res. 5(3): 177-182.

Histological Evaluation

ROE samples subjected to histological analysis were fixed overnight in a freshly prepared Karnovsky solution (2.0% paraformaldehyde, 2.0% glutaraldehyde in 0.1 M sodium cacodylate buffer).

After rinsing in the buffer, the samples were stained with 2% of $OsO_4$ and 2% of uranyl acetate. The samples were then dehydrated in acetone solutions and incorporated into Epon-Araldite resin (Fluka, Italy). Cross sections of 0.5 microns, subjected to toluidine blue staining, of all the samples of the different experimental groups were prepared and then observed by optical microscopy (Pro Plus Imaging software) at a final magnification of 1500×, and by TEM (Zeiss microscope EM10).

Results

MTT Test

Figure 3:
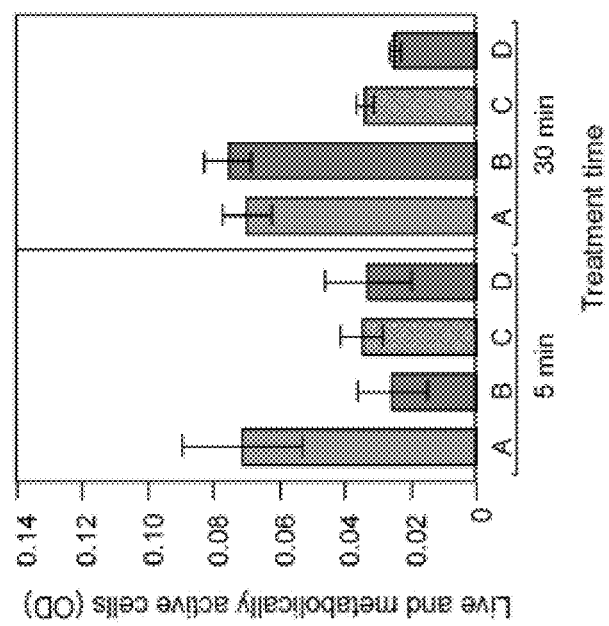
FIG. 3 shows the results of the MTT viability test on ROE cells after 1 minute of treatment with a 3% solution by volume $H_2O_2$ and subsequent different treatment times with the solutions A, B, C and D according to Example 1.
Figure 2:
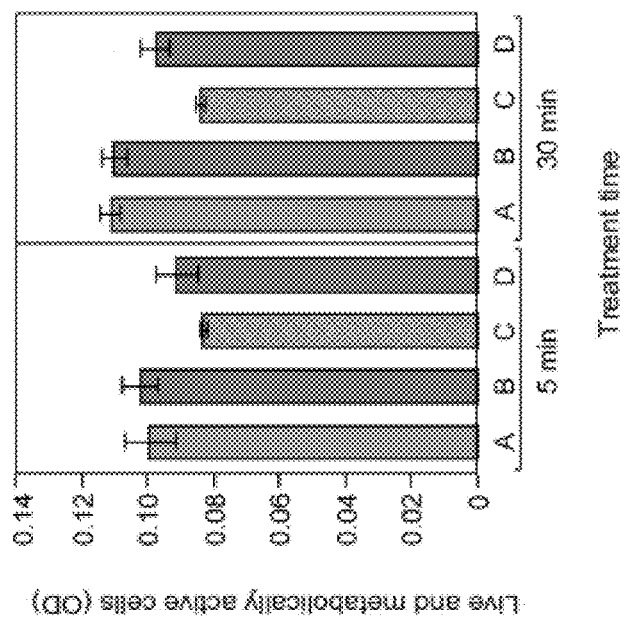
FIG. 2 shows the results of the MTT viability test on ROE cells at different treatment times with the solutions A, B, C and D according to Example 1.

The dataset of the MTT viability test was preliminarily checked for distribution normality (Shapiro-Wilk test) and homoscedasticity (Levene test). Since the data were not normally distributed even after logarithmic transformation, the nonparametric analysis was performed using the Wilcoxon test (p<0.05). The results obtained on ROE cells at different treatment times with the solutions A, B, C and D are shown in FIG. 2. FIG. 3 shows the results of the MTT viability test on ROE cells after 1 minute of treatment with a 3% solution by volume $H_2O_2$ and subsequent different treatment times with the solutions A, B, C and D.

As can be seen in FIG. 2, after 5 minutes of treatment with the mouthwash solutions, a significant decrease in viability was observed in samples treated with the solution C compared with the solution B. No significant change in the viability of the solutions was identified with respect to the negative control (solution D). Treating the ROE samples with the mouthwash solutions for 30 minutes resulted in a significant reduction in viability by means of the solution C with respect to the solutions containing chlorhexidine. The treatment with 3% by volume of $H_2O_2$ (FIG. 3) led to a general decrease in viability. The samples treated for 5 minutes showed a significantly greater viability after the treatment with the solution A than with the solution B but, after 30 minutes of treatment, the difference between these two solutions decreased significantly and was significantly greater than with the solutions C and D. In addition, the solution C elicited significantly greater viability than the solution D, suggesting a significant and positive activity of NaDNA on cell viability.

CLSM Observations

Figure 4:
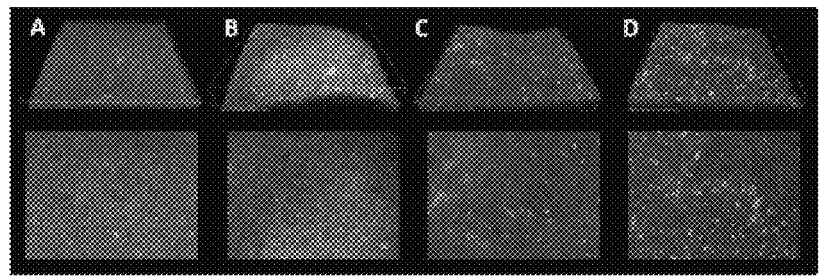
FIG. 4 shows 3D rendered reconstructions of the CLSM observations and the projections of the maximum intensity of the ROE samples, after 30 minutes of treatment respectively with the solutions A, B, C and D according to Example 1.
Figure 5:
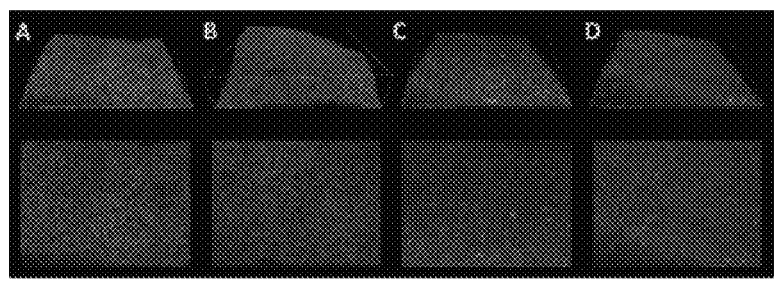
FIG. 5 shows 3D rendered reconstructions of the CLSM observations and the projections of the maximum intensity of the ROE samples, after 1 minute of treatment with a 3% solution by volume of $H_2O_2$ and subsequent 30 minutes of treatment respectively with the solutions A, B, C and D according to Example 1.

Confocal microscopy reconstructions obtained after a 5-minute treatment with the mouthwash solutions showed no differences between the groups. The reconstructions of samples after 30 minutes of treatment are shown in FIG. 4 (samples after 30 minutes of treatment with the solutions A, B, C and D) and in FIG. 5 (samples after 1 minute of treatment with $H_2O_2$ and subsequent 30 minutes of treatment with the solutions A, B, C and D).

The samples treated with the solution A and, to a lesser extent, with the solution B showed a good preservation of the cell structure even in samples exposed to hydrogen peroxide. The negative control samples (D) showed the presence of dead cells on the surface and, after the treatment with hydrogen peroxide, a layer almost completely composed of dead cells was identifiable on the surface. The samples treated with only NaDNA (solution C) showed a much lower amount of dead cells than in the negative control either in the absence or presence of hydrogen peroxide treatment.

Histological Evaluation

The sections of the ROE tissue (0.5 µm) obtained after the 5-minute treatment with the mouthwash solutions showed no differences between the groups. The sections of the samples after 30 minutes of treatment are shown in FIG. 6 (samples treated with the solutions A, B, C and D) and in FIG. 7 (samples after 1 minute of treatment with $H_2O_2$ and subsequent treatment with the solutions A, B, C and D).

Figure 6:
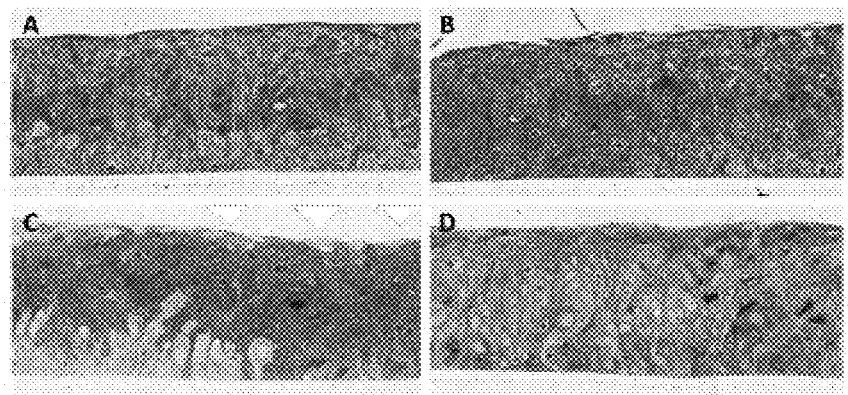
FIG. 6 shows sections of ROE samples after 30 minutes of treatment respectively with the solutions A, B, C and D according to Example 1.
Figure 7:
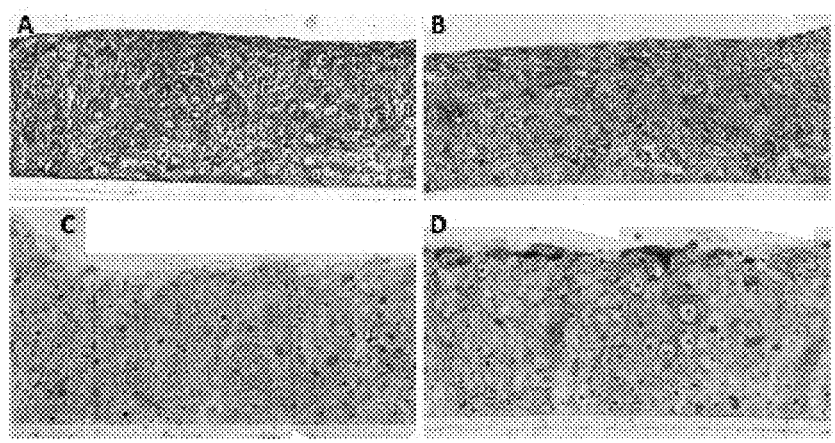
FIG. 7 shows sections of ROE samples after 1 minute of treatment with a 3% solution by volume of $H_2O_2$ and subsequent 30 minutes of treatment respectively with the solutions A, B, C and D according to Example 1.

Considering the samples of FIG. 6, the negative control (D) showed the complete preservation of the tissue structures. The samples treated with the solutions A and, to a lesser extent, B showed alterations of the cell structure, such as vacuolisation, the degenerated nucleus and the initial enlargement of the intercellular spaces, both in the outermost and basal layers. These alterations may be due to the activity of chlorhexidine. In fact, the addition of NaDNA to the chlorhexidine mouthwash (solution B) showed less intense alterations of the cell structure with respect to the mouthwash with chlorhexidine only (solution A). The samples treated with the solution C showed the same alterations, but limited to the first cell layer. The treatment with hydrogen peroxide (see FIG. 7) showed, as expected, an extensive damage to ROE cells, such as marked vacuolisation, the degenerated nucleus and the widening of intercellular spaces. These alterations were more evident in the samples treated with the negative control (D) and with the solution A (chlorhexidine only). In the samples treated with the solution B, some cells that show no signs of degeneration can be found in the innermost layers, where these cells were probably more protected from reactive oxygen species generated by hydrogen peroxide and where NaDNA exerted an action of cell damage minimization. The samples treated with the mouthwash C (NaDNA only) showed minimal signs of cell degeneration.

In conclusion, NaDNA showed a clear protective action against cell degeneration due to the oxidative stress and the exposure to the mouthwash solutions containing only chlorhexidine.

Example 2

The purpose of this experiment is to test the effectiveness of the oral care product according to the present invention in the form of a gel in the presence of peri-implant mucositis, i.e. in the presence of bleeding on probing around an implant in the absence of loss of support bone and pathological pockets (<3 mm).

Selection of Patients

The study was conducted in compliance with the criteria of the Declaration of Helsinki and according to the principles of Good Clinical Practice following approval by the Ethics Committee for Biomedical Research in Chieti and Pescara. Therefore, patients with peri-implant mucositis were recruited at the Department of Medical, Oral and Biotechnological Sciences for the purpose of evaluating the control properties of bacterial plaque and inflammation.

The patients selected for the study were enrolled in accordance with the principles enshrined in the Declaration of Helsinki for conducting scientific studies, and according to the following inclusion criteria:

Patients in good health therefore absence of: relevant systemic diseases, such as primarily diabetes, immune diseases, hematological diseases; neoplasms; serious infectious diseases such as HIV or viral hepatitis with signs and/or symptoms of liver failure; cognitive difficulties; intellectual difficulties; motor deficits;

Over 18 years old;

Participation in the experimentation through a specific informed consent;

Candidates selected for the presence of an implant affected by mucositis, defined as:

presence of bleeding on probing in the absence of loss of support bone around the implant;

Absence of plant mobility;

Presence of at least 2 mm of keratinized gingiva around the implant;

Absence of implant rehabilitations other than single crowns or bridges of maximum three elements;

Absence of evident signs of overload or occlusal trauma.

The exclusion principles will be as follows:

No total edentulous after the implant surgical procedure (if there are no natural elements after surgery, it is impossible to determine the plaque, bleeding variables);

Non-smokers or light smokers (less than 10 cigarettes per day);

Good oral care with low plaque and bleeding index levels and absence of periodontal lesions on other dental elements (FMPS and FMBS≤25%);

Patients allergic to chlorhexidine gluconate or other components of the formulation of the device and placebo.

Choice of Primary Evaluation Index

Primary Objectives: Plaque index score: the presence/absence of plaque was recorded on the surfaces evaluated.

Choice of Secondary Evaluation Index

Recording of clinical parameters of

Bleeding on probing ("BOP"): the presence/absence of bleeding on probing was recorded.

Gingival Index (Loe & Silness 1963): the health of periodontal tissues was recorded according to the following criterion:

0=Normal gingiva;

1=Mild inflammation—slight edema and colour change in the absence of bleeding on probing;

2=Moderate inflammation—reddened, edematous tissues and bleeding on probing;

3=Severe inflammation—marked redness, edema, ulceration and bleeding tendency.

Statistical Analysis

Descriptive data analysis was carried out, where quantitative variables are presented with mean and standard deviation. To compare the two groups examined with regard to the quantitative variables, the Student's T test is used. The significance level is set at 5%. The normal distribution was evaluated by means of the Kilmogorov Smirnoff test (p-value>0.05) and by evaluating the graphs with the 14-day response variables.

Experimental Phases

The following gels have been tested:
E. gel containing 0.2% by weight of chlorhexidine and 0.01% by weight of NaDNA;
F. "placebo" gel with composition identical to gel E but not containing neither chlorhexidine nor NaDNA;

The sample size was 24 patients, with an enrollment ratio between the two groups of 1:1 (12 patients per experimental group).

After recording the clinical variables and an oral care session, each patient received an anonymous gel tube, a syringe and an applicator nozzle for applications (3 times a day for 14 days). The patients who received the gel E (containing 0.2% by weight of chlorhexidine and 0.01% by weight of NaDNA), were identified as Group A, the patients who received the gel F ("placebo" gel), were identified instead as Group B.

The check-ups with the values to be recorded during the follow-ups were set up as follows:
Baseline (Time 0, "T0")
14 days post-surgery (Time 1, "T1")

In phase T0, the periodontal record was created with the collection of the Plaque Index, Bleeding on Probing, and the Gingival Index as per clinical protocol.

All patients who completed the T0 and T1 clinical study phase. The subjects were therefore instructed on the correct home oral care maneuvers and re-evaluated after 14 days. In phase T1, the periodontal record was created with the collection of the Plaque Index, Bleeding on Probing, and the Gingival Index as per clinical protocol. No adverse effects were recorded during the study period. Furthermore, there were no unwanted effects or side effects following the administration of gel E or F.

Results

Primary Valuation Indices

At time T0, the baseline relative to the Plaque Index detected of 2.4±0.4 for Group A (gel E) and 2.2±0.5 for Group B (gel F) (p>0.05). After 2 weeks of treatment (T1) the measured Plaque Index is 0.5±0.4 for Group A (gel E) and 1.7±1.9 for Group B (gel F) (p<0.05).

Secondary Valuation Indices

At time T0, the baseline relative to the BOP detected of 57.1%±15.2% for Group A (gel E) and 55.3%±11.7% for Group B (gel F) (p>0.05). After 2 weeks of treatment (T1) the measured BOP is 14.3%±6.6% for Group A (gel E) and 45.4%±9.8% for Group B (gel F) (p<0.05).

The data relative to the Gingival Index measured at the different experimental times: at the Baseline, and at T1 after two weeks of treatment are shown in Table 1.

TABLE 1

| | Group A (gel E) | Group B (gel F) | P value |
|---|---|---|---|
| Gingival Index T0 | 2.21 ± 0.51 | 2.35 ± 0.67 | p > 0.05 |
| Gingival Index T1 | 0.82 ± 0.53 | 1.62 ± 0.74 | p < 0.05 |

Conclusions

At the experimental time T1 a statistically significant difference emerges between Group A (gel E) and Group B (gel F) with regard to the primary Plaque Score parameter. The benefits of the treatment are also evident in relation to the secondary indices of the Bleeding on Probing and the Gingival Index, from which a statistically significant difference of the evaluated parameters emerges in favor of Group A, thus confirming the effectiveness of the oral care product according to the present invention in the treatment of peri-implant mucositis.

Example 3

The purpose of this experiment is to clinically evaluate the antimicrobial and control properties of the dental plaque of the oral care product according to the present invention in the form of mouthwash on the soft tissue of the oral cavity after two weeks on patients with periodontal pathology.

Selection of Patients

The experiment was conducted in compliance with the criteria of the Helsinki Declaration and according to the principles of Good Clinical Practice following approval by the Ethics Committee for Biomedical Research in Chieti and Pescara. Therefore, patients with periodontal disease were recruited at the Department of Medical, Oral and Biotechnological Sciences for the purpose of evaluating the control properties of bacterial plaque and gingival inflammation.

Patients were recruited according to the following inclusion criteria:
Patients with chronic periodontitis with probings>3 mm on a number greater than or equal to 20 elements;
Non-smoking or moderately smoking patients (<10 cigarettes per day);
The exclusion criteria were as follows:
Patients with orthodontic devices;
Intolerances or allergies to mouthwashes;
Tobacco smoking and alcohol consumption;
Patients undergoing radiation therapy/chemotherapy for less than 5 years;
Immunocompromised patients;
Systemic, kidney or cardiovascular diseases;
Pregnant, breastfeeding women or undergoing antibiotic and anti-inflammatory therapy.

Choice of Primary Evaluation Index

Full mouth plaque score (FMPS): the presence/absence of plaque in 4 sites per tooth will be recorded and the percentage will be calculated in relation to the surfaces Choice of Secondary Evaluation Index Full mouth bleeding score (FMBS): the presence/absence of bleeding will be recorded on probing at 4 sites per tooth and the percentage in relation to the surfaces is calculated.

Gingival Index (Loe & Silness 1963): the health of periodontal tissues is recorded according to the following criterion:
0=Normal gingiva;
1=Mild inflammation—slight edema and colour change in the absence of bleeding on probing;
2=Moderate inflammation—reddened, edematous tissues and bleeding on probing;
3=Severe inflammation—marked redness, edema, ulceration and bleeding tendency.

Recording of any Complications, Adverse Events and Drop Outs.

Statistical Analysis

The distribution of FMPS, FMBS and GI data relative to the experimental groups at different experimental times such as baseline, 1 week and 2 weeks, were evaluated by Kolmogorov-Smirnov Test. The significance of the study data was evaluated by Student's T test for p<0.05.

Experimental Treatment

The following mouthwashes have been tested:
G: mouthwash containing 0.2% by weight of chlorhexidine and 0.01% by weight of NaDNA;
H: "placebo" mouthwash with composition identical to gel E but containing neither chlorhexidine nor NaDNA.

The sample size was 54 patients, with an enrollment ratio between the two groups of 1:1 (27 patients per experimental group).

The patients who received the mouthwash G (containing 0.2% by weight of chlorhexidine and 0.01% by weight of NaDNA) were identified as Group A, the patients who received the mouthwash H ("placebo" mouthwash), were identified as Group B.

Study Phases

Experimental phase V1. Screening check-up to evaluate patient eligibility and study inclusion. Approval of informed consent and oral care instructions.

Experimental phase V2 (baseline). Periodontal record with recording of the Full Mouth Plaque Score (FMPS) and the Full Mouth Bleeding Score (FMBS) and Gingival Index (GI). Patients will be given the package of mouthwash in relation to the assigned study group (A or B) and a 10 ml rinse will be performed. The protocol included a total of three home rinses per day (morning and evening after meals) for 2 weeks of treatment.

Experimental phase V3 (1 week) Control with recording of the following FMPS, FMBS and GI indices.

Experimental phase V4 (2 weeks) Control with recording of FMPS, FMBS, GI, and finishing in order to remove possible spots that have formed.

Results

Primary Valuation Indices

At time V2, the baseline relative to the FMPS detected was found to be 52.7±9.2 for Group A (mouthwash G) and 58.2±6.1 for Group B (mouthwash H) ($p>0.05$). At 1 week of treatment (V3) the measured FMPS was found to be 13.3±5.6 for Group A and 18.7±4.3 for Group B ($p<0.05$). Finally, at 2 weeks of treatment (V4) the FMPS was found to be 14.2±4.1 for Group A and 20.3±5.2 for Group B ($p<0.05$).

Secondary Valuation Indices

At time V2, the baseline for the FMBS detected was found to be 46.7±8.7 for Group A and 49.2±6.2 for Group B ($p>0.05$). At 1 week of treatment (V3) the measured FMPS was found to be 12.7±4.2 for Group A and 18.5±5.9 for Group B ($p<0.05$). Finally, at 2 weeks of treatment (V4) the FMBS was found to be 13.1±3.2 for Group A and 19.8±4.9 for Group B ($p<0.05$).

The data relative to the Gingival Index measured at the different experimental times: at the Baseline, at 1 week and at 2 weeks are presented in Table 2.

TABLE 2

|  | Group A (mouthwash G) | Group B (mouthwash H) | P value |
| --- | --- | --- | --- |
| Gingival Index V2 (baseline) | 2.85 ± 0.47 | 2.71 ± 0.51 | p > 0.05 |
| Gingival Index V3 (1 week) | 1.14 ± 0.55 | 1.75 ± 0.49 | p < 0.05 |
| Gingival Index V4 (2 weeks) | 1.09 ± 0.44 | 1.96 ± 0.39 | p < 0.05 |

Conclusions

Already at the experimental time V3 a statistically significant difference emerges between Group A and Group B with regard to the primary parameter FMPS. Which evidence is confirmed after two weeks of treatment, in which the average FMPS levels remain below 20% in Group A. In this regard, the benefits of the treatment are also evident in relation to the secondary indices of the FMBS and the Gingival Index which show a statistically significant variation of the clinical parameters in favor of Group A, evidence correlable to the beneficial effect induced by the oral care product according to the invention on the gingival tissues of the subjects undergoing treatment.

The invention claimed is:

1. A method for treatment of side effects of chlorhexidine in a patient undergoing chlorhexidine treatment, the method comprising:
   administering to said patient an oral care product consisting of, comprising with respect of the total weight of the oral care product: from 0.01% to 1.0% by weight of chlorexidine, from 0.01% to 0.3% by weight of sodium DNA, from 0.1% to 0.5% by weight of at least one metabisulfite salt of an alkaline or an alkaline earth metal and from 0.1% to 1.% by weight ascorbic acid, and one or more additive selected from the group consisting of sweeteners, flavorings, wetting agents, preservatives, solubilizing surfactants, pH regulators, water, polyvinyl pyrrolidone-vinyl acetate copolymer, hydroxyethyl cellulose, carboxymethyl cellulose, sodium acetate, acetic acid, silica, glycerol, cocamidopropyl betaine, and food coloring, wherein said side effects are selected from the group consisting of
   alteration of cell structure of oral mucosa of said patient, said alteration of the cell structure being selected from the group consisting of vacuolisation, degeneration of cell nucleus and expansion of intercellular spaces and dark pigmentation on teeth.

2. The method according to claim 1, wherein said oral care product is selected from the group consisting of: mouthwash, periodontal gel, and toothpaste.

3. The method according to claim 2, wherein said oral care product is a mouthwash and chlorhexidine is in a form of a salt or a complex.

4. The method according to claim 2, wherein said oral care product is a mouthwash, wherein said mouthwash consists of water, xylitol, propylene glycol, Hydrogenated castor oil PEG 40, Ascorbic acid, Chlorhexidine digluconate, Polyvinylpyrrolidone-vinylacetate copolymer, Sodium DNA, Flavouring, Poloxamer 407, Sodium metabisulfite, Sodium citrate, Citric acid, CI 42090 and CI 17200.

5. The method according to claim 4, wherein said at least one polyvinyl pyrrolidone-vinyl acetate copolymer is present in an amount of from 0.05% to 1% by weight, with respect to a total volume of the mouthwash.

6. The method according to claim 2, wherein said oral care product is a periodontal gel.

7. The method according to claim 2, wherein said oral care product is a toothpaste.

8. The method according to claim 1, wherein said chlorhexidine treatment is for the treatment of at least one pathology selected from the group consisting of: gingivitis, bacterial plaque, and periodontitis.

9. The method according to claim 1, wherein said sweeteners is selected from the group consisting of xylitol, sodium saccharinate, potassium acesulfame, sucralose and *Stevia* extract.

10. The method according to claim 1, wherein said flavorings is selected from the group consisting of peppermint, menthol, anethole, *Mentha viridis*, cinnamon, cloves and eucalyptol.

11. The method according to claim 1, wherein said wetting agents is selected from the group consisting of propylene glycol, sorbitol and glycerin.

12. The method according to claim 1, wherein said preservatives is selected from the group consisting of sodium benzoate and methylisothiazolinone.

13. The method according to claim 1, wherein said solubilizing surfactants is selected from the group consisting of hydrogenated castor oil PEG 40 and Poloxamer 407.

14. The method according to claim 1, wherein said pH regulators is selected from the group consisting of sodium citrate and citric acid.

15. The method according to claim 1, wherein said food coloring is selected from the group consisting of CI 19140, CI 42090 and CI 17200.

16. The method according to claim 2, wherein said oral care product is a toothpaste, wherein said toothpaste consists of water, xylitol, Hydrogenated castor oil PEG 40, Ascorbic acid, Chlorhexidine digluconate, Polyvinylpyrrolidone-vinylacetate copolymer, Sodium DNA, Flavouring, Sodium metabisulfite, Sodium citrate, sorbitol, silica, glycerol, cocamidoproyl betaine, carboxymethyl cellulose, sodium saccharine and sodium benzoate.

17. The method according to claim 2, wherein said oral care product is a periodontal gel, wherein said periodontal gel consists of water, Hydrogenated castor oil PEG 40, Ascorbic acid, Chlorhexidine digluconate, Polyvinylpyrrolidone-vinylacetate copolymer, Sodium DNA, Sodium metabisulfite, propylene glycol, hydroxyethyl cellulose, sodium acetate, menthol, peppermint oil and acetic acid.

* * * * *